United States Patent
Al Ahmad

(10) Patent No.: US 10,942,110 B2
(45) Date of Patent: Mar. 9, 2021

(54) SYSTEM AND METHOD FOR DETECTING ABNORMALITIES IN CELLS

(71) Applicant: UNITED ARAB EMIRATES UNIVERSITY, Al Ain (AE)

(72) Inventor: Mahmoud F. Y. Al Ahmad, Al Ain (AE)

(73) Assignee: UNITED ARAB EMIRATES UNIVERSITY, Al Ain (AE)

(*) Notice: Subject to any disclaimer, the term of this patent is extended or adjusted under 35 U.S.C. 154(b) by 449 days.

(21) Appl. No.: 15/624,095

(22) Filed: Jun. 15, 2017

(65) Prior Publication Data

US 2018/0364143 A1    Dec. 20, 2018

(51) Int. Cl.
*G01N 15/10* (2006.01)
*B01L 3/00* (2006.01)
(Continued)

(52) U.S. Cl.
CPC ...... *G01N 15/1056* (2013.01); *B01L 3/50273* (2013.01); *B01L 3/502715* (2013.01);
(Continued)

(58) Field of Classification Search
CPC .......... G01N 15/1056; G01N 15/1031; G01N 27/02; G01N 33/50; G01N 33/5438;
(Continued)

(56) References Cited

U.S. PATENT DOCUMENTS

| 6,373,682 | B1 | 4/2002 | Halden et al. |
| 2003/0080442 | A1* | 5/2003 | Unger .............. B01L 3/5025 |
| | | | 257/787 |

(Continued)

FOREIGN PATENT DOCUMENTS

| CN | 101625358 A | 1/2010 |
| CN | 203988365 | 12/2014 |

(Continued)

OTHER PUBLICATIONS

EPO, Partial European Search Report, dated Aug. 2, 2018, re European Patent Application No. 18178004.0.

(Continued)

*Primary Examiner* — Robert J Eom
(74) *Attorney, Agent, or Firm* — Perry + Currier Inc.; Alan F. Feeney

(57) ABSTRACT

A system and method for detecting particles in a fluidic medium using a microfluidic sensor is described. The system utilises microfluidic channels though which the fluidic medium is passed. On one section of the microfluidic channel, an array of non-flexible electrodes are coupled with uniform spacing therebetween. On the opposing section of the channel, a flexible electrode is coupled and all electrodes are connected to an electrical analyser which is used to generate an electrical field inside the microfluidic channel with the flexible electrode acting as ground. The flexible electrode is actuated by different means to narrow the width of the microfluidic in the section of interest and to capture the particle between the section, where sectional scans of the particles are obtained and electrical properties of the particle are measured, thereby detecting the particles in the fluidic medium.

15 Claims, 5 Drawing Sheets

(51) Int. Cl.
*G01N 33/50* (2006.01)
*G01N 33/543* (2006.01)
*G01N 27/02* (2006.01)
*G01N 35/10* (2006.01)
*G01N 15/00* (2006.01)
*G01N 35/00* (2006.01)

(52) U.S. Cl.
CPC .... *B01L 3/502761* (2013.01); *G01N 15/1031* (2013.01); *G01N 27/02* (2013.01); *G01N 33/50* (2013.01); *G01N 33/5438* (2013.01); *G01N 35/10* (2013.01); *B01L 2200/0647* (2013.01); *B01L 2200/0668* (2013.01); *B01L 2300/044* (2013.01); *B01L 2300/0645* (2013.01); *B01L 2300/123* (2013.01); *B01L 2400/0481* (2013.01); *B01L 2400/0487* (2013.01); *B01L 2400/0655* (2013.01); *G01N 2015/0019* (2013.01); *G01N 2015/0038* (2013.01); *G01N 2015/0065* (2013.01); *G01N 2015/1006* (2013.01); *G01N 2035/00237* (2013.01); *G01N 2035/1034* (2013.01)

(58) Field of Classification Search
CPC ........... G01N 35/10; G01N 2015/0019; G01N 2015/0038; G01N 2015/0065; G01N 2015/1006; B01L 3/502715; B01L 3/50273; B01L 3/502761; B01L 2200/0647; B01L 2200/0668; B01L 2300/044; B01L 2300/0645; B01L 2300/123; B01L 2400/0481; B01L 2400/0487; B01L 2400/0655; H01N 2035/00237
See application file for complete search history.

(56) References Cited

U.S. PATENT DOCUMENTS

| | | |
|---|---|---|
| 2004/0257745 A1 | 12/2004 | Robert |
| 2005/0223783 A1 | 10/2005 | Spivak |
| 2008/0050769 A1 | 2/2008 | Huang et al. |
| 2008/0248960 A1 | 10/2008 | Hong et al. |
| 2010/0015614 A1* | 1/2010 | Beer ................. B01L 3/502792 435/6.12 |
| 2016/0158757 A1 | 6/2016 | Breinlinger et al. |

FOREIGN PATENT DOCUMENTS

| | | |
|---|---|---|
| WO | WO-2005030822 A2 | 4/2005 |
| WO | WO-2015116083 A1 | 8/2015 |
| WO | WO-2016161400 A1 | 10/2016 |

OTHER PUBLICATIONS

EPO, Extended European Search Report, dated Nov. 9, 2018, re European Patent Application No. 18178004.0.

EPO, Communication pursuant to Article 94(3) EPC, dated Sep. 24, 2019, re European Patent Application No. 18178004.0.

* cited by examiner

US 10,942,110 B2

SYSTEM AND METHOD FOR DETECTING ABNORMALITIES IN CELLS

TECHNICAL FIELD

This invention relates generally to a system and method for detecting particles in a fluidic medium and more specifically, to a system comprising micro-sensors and microfluidic channels and method of using same for identifying electrical properties of particles passed through the microfluidic channels to allow for detection of such particles.

BACKGROUND

Biomarkers and Enzyme-Linked Immunosorbent Assay (ELISA) kit are usually used to detect and quantify the viruses inside a cell blood suspended samples. Polymerase chain reaction (PCR) based technologies, remain the gold standard for the detection and identification of many DNA and RNA viruses. Although very sensitive, these approaches are time consuming and expensive.

There is a desire in the field for the development of sensors and sensing techniques to develop alternative user friendly detection methods that are more efficient and yield results faster than the traditional ones available in the field.

SUMMARY OF THE INVENTION

The current disclosure has several aspects. In one aspect of the invention, a microfluidic sensor for detecting particles in a fluidic medium is provided. The microfluidic sensor includes a microfluidic channel having a width through which the fluidic medium in passed. The microfluidic channel has a flexible membrane. An array of non-flexible electrodes is coupled to a first section of the microfluidic channel. The array of electrodes has spacing between each electrode of the electrodes array. A flexible electrode is coupled to a second section of the microfluidic channel opposite to the array of non-flexible electrodes. An electrical analyser is in electrical communication with each electrode of the non-flexible array of electrodes and the flexible electrode. The electrical analyser applies an electrical potential between each of the electrodes in the electrode array to generate an electrical field inside the microfluidic channel with the flexible electrode acting as ground. The sensor also includes means for actuating the flexible electrode to narrow the width of the microfluidic channel between the first section and second section and to capture the particle between the first section and the second section of the microfluidic channel, where electrical properties of the particle are measured. This allows for detecting the particle in the fluidic medium.

In a related embodiment, the microfluidic sensor further includes a pump for pumping the fluidic medium through the microfluidic channel to an area where the particle in the fluidic medium is captured.

In a related embodiment, the microfluidic sensor further includes a controller for controlling any one of electrical potential applied by the analyser, volume flow of the fluidic medium, or rate of pumping the fluidic medium through the microfluidic channel.

In a related embodiment, the means for actuating the flexible electrode includes an electrostatic electrode resting on a substrate away from the microfluidic channel. The electrostatic electrode are in electrical communication with the controller and controller applies an electrostatic biasing between the flexible electrode and the electrostatic electrode to cause the flexible electrode to flex and narrow the microfluidic channel.

In another embodiment, the microfluidic sensor is provided, where the means for actuating the flexible electrode comprises a piezoelectric sheet sandwiched between the flexible electrode and a second electrode. The second electrode is in electrical communication with the controller. The controller applies a potential difference between the second electrode and the flexible electrode causing the piezoelectric sheet to move thereby flexing the flexible electrode to narrow the microfluidic channel.

In another embodiment, a microfluidic sensor is provided, where the means for actuating the flexible electrode comprises a second microfluidic chamber sandwiched between the flexible electrode and a fixed side. A second pump is used for pumping pressure fluid into the second microfluidic chamber. The second pump is in electrical communication with the controller, and the controller controls the flexible electrode to flex which leads to narrowing the microfluidic channel by controlling through the second pump the flow rate, volume and timing of the pressure fluid into the second microfluidic chamber.

In a related embodiment, when the flexible electrode is not flexed, the microfluidic channel is dimensioned to be bigger in diameter than the particle and when the flexible electrode is flexed, the microfluidic channel is dimensioned to be substantially equal in diameter to the particle. This causes a tight fit of the particle between the first and second section of the microfluidic channel.

In a related embodiment, the particle is described to be one of a virus, a cell, an exosome or other biological or non-biological material.

In a related embodiment, the spacing between each electrode of the electrode array is uniform.

In a related embodiment, when the particle is a cell, the spacing is less than a diameter of the cell and when the particle is one of an exosome, bacteria or a virus, the spacing is substantially equal to the particle.

In a related embodiment, 4, the particle is a cell. The controller also controls holding the cell stationary between the first section and the second section until measurement of electrical properties of a part of the cell is completed between two adjacent electrodes of the electrodes array. The controller further controls a discrete movement of the cell through a tight fit spacing between the first section and the second section of the microfluidic channel to scan a next part of the cell thereby creating discrete sectional scanning of the cell.

In another aspect of the invention, a microfluidic sensor for detecting a particle having a known size in a fluidic medium is described. The microfluidic sensor includes a nonflexible microfluidic channel having a width through which the fluidic medium is passed. The microfluidic channel has a narrower section and a wide section. The wide section is dimensioned to be more in diameter than the particle's known size and the narrow section is dimensioned to be less in diameter than the particle's known size such that the particle is captured in the narrow section when pushed through it. Array of electrodes is coupled to a first section of the narrow section of the microfluidic channel. The array of electrodes has spacing between each electrode of the electrodes array. A ground electrode is coupled to a second section of the narrow section of the microfluidic channel opposite to the array of electrodes. An electrical analyser is in electrical communication with each electrode of the array of electrodes and the ground electrode. The electrical analyser applies an electrical potential between each of the electrodes in the electrode array to generate an electrical field inside the narrow section with the ground electrode acting as ground; wherein electrical properties of the captured particle are measured, thereby detecting the particle in the fluidic medium.

In another aspect of the invention, a method of detecting a particle in a fluidic medium using a microfluidic sensor is described. The method includes passing the fluidic medium through a flexible microfluidic channel of the micro sensor, where the flexible microfluidic channel has an array of non-flexible electrodes uniformly spaced apart and coupled to a first section of the microfluidic channel, and a flexible electrode coupled to a second section of the microfluidic channel opposite to the array of non-flexible electrodes. The method also includes controlling movement of the flexible electrode to narrow a width of the microfluidic channel and to capture the particle between the first section and the second section; The method further includes generating electrical field between electrodes of the electrode array spaced apart; scanning a section of the particle between two electrodes of the electrode array while the particle is captured between the first section and the second section using the electrical field generated. The method also includes incrementally moving the captured particle through the microfluidic channel and scanning a section of the particle between two electrodes of the electrode array using the electrical field generated after each incremental move until the particle entirely passes through; and using the sectional scans to detect and identify the particle.

In a related embodiment, the method further includes using a plurality of control samples of fluidic medium, each having known particles therein; generating sectional scans for the particle in each control sample; and storing the generated sectional scans comprising electrical properties of each particle in a lookup table.

In a related embodiment, the method further includes identifying a particle in an unknown sample by comparing the sectional scans of the particle therein and matching them to values obtained from the lookup table.

Other aspects of the invention will be apparent as will be shown in the detailed description of the invention.

BRIEF DESCRIPTION OF THE DRAWINGS

The accompanying drawings illustrate non-limiting example embodiments of the invention.

DETAILED DESCRIPTION

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

This current disclosure presents a system comprising a micro-sensing device and method of operating same, where the system utilizes microfluidic channels for the detection of abnormalities in biological entities immersed in a fluidic sample by measuring the electrical properties of individual biological entities disposed in the fluidic sample. Such system may be used in a wide verity of applications including in the medical field. The current disclosure further describes a system comprising micro-sensors and method of operating same in which biological, organic or non-organic particles in a fluidic medium are passed through microfluidic channels and where electrical properties of the particles are measured, characterized and analyzed by the micro-sensors to determine physical properties and changes thereof of the particles.

Microfluidics deals with the behaviour, precise control and manipulation of fluids that are geometrically constrained to a small, typically sub-millimeter, scale. Fluids behave very differently on the micrometric scale than they do in everyday life. Microfluidic devices exploit the physical and chemical properties of liquids and gases at the microscale. They offer several benefits over conventionally sized systems. Microfluidics allows the analysis and use of less volume of samples, chemicals and reagents reducing the global fees of applications.

Figure 1:
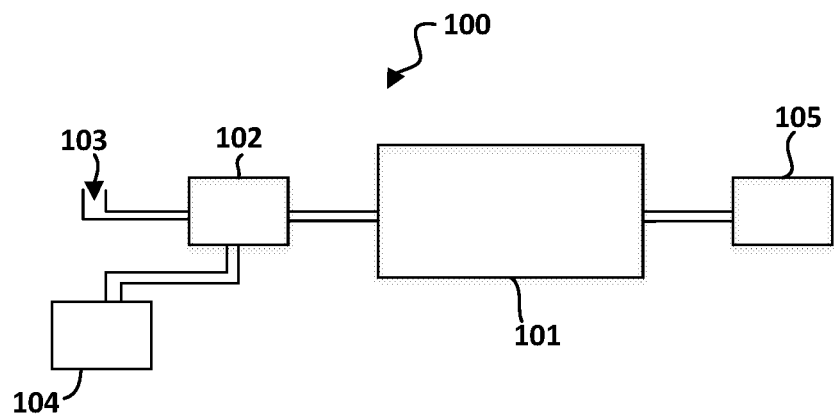
FIG. 1 shows a schematic view of a system utilizing micro-sensing structure according to an exemplary embodiment of the present invention.

Referring to FIG. 1, a schematic view of an electrical sensing system 100 is illustrated in accordance with an exemplary embodiment of the present invention.

System 100 includes a micro-sensing structure 101, the content of which will be described in detailed below. Micro-sensing structure 101 is in fluid communication with a main pump 102 for pumping a fluidic medium into the micro-sensing structure 101. The fluidic medium may be any fluidic medium known in the art for carrying biological, organic or non-organic particles. By way of non-limiting example, the fluidic medium may be Water, Dulbecco's Modified Eagle's Medium (DMEM), phosphate buffered saline (PBS), or any other relevant medium used for cell culture. Particles carried by the fluidic medium may be cells, viruses, bacteria, exosomes or other biological, or non-biological particles of interest. The fluidic medium is deposited into a depositing chamber 103, which is in fluid communication with main pump 102.

Main pump 102 is controlled by a master controller 104. Master controller 104 may be any known controller known in the art comprising a processor (not shown). For example, master controller 104 may be a computer that is configured to control multiple parameters including but not limited to the operation of main pump 102 in system 100, the volume flow of fluidic medium and the time for pumping the fluidic medium from the depositing chamber 103 to the micro-sensing structure 101.

Micro-sensing structure 101 is also in fluid communication with disposition chamber 105 into which the fluidic medium is disposed of once passed through the micro-sensing structure 101, where detection and analysis is conducted, as will be described below.

Figure 2:
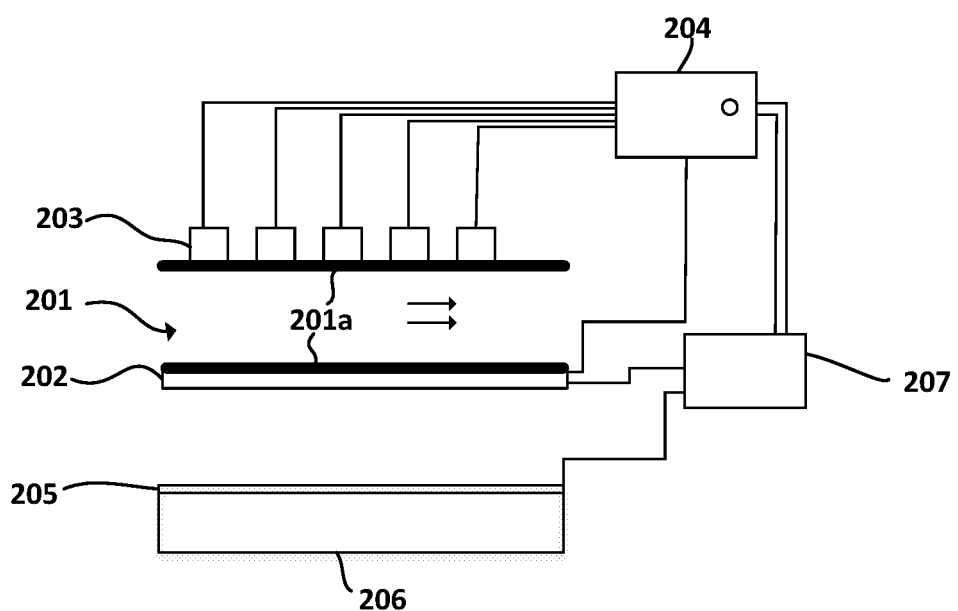
FIG. 2 shows a cross-sectional view of a sensor device utilizing microfluidic channels according to an exemplary embodiment of the present invention.

FIG. 2 shows a cross-sectional view of micro-sensing structure 101 in FIG. 1 according to one embodiment of the present disclosure. The structure comprises a section of microfluidic channel 201 through which the fluidic medium pumped into the micro-sensing structure 101 by main pump 102 passes. Structure 101 may comprise more than one microfluidic channel 201. The microfluidic channel in this embodiment is shown to be substantially straight. However, it is to be understood that micro-fluidic channel 201 may have different uniform or non-uniform shapes known in the art. Microfluidic channel 201 may be made from material such as polydimethylsiloxane (PDMS), Glass, silicone (Si) or any other sacrificial materials that used in Microelectromechanical systems (MEMS)/NEMS and micromachining technologies. The walls 201a of microfluidic channel 201 are flexible such that sections of the walls may be compressed to cause the spacing inside the microfluidic channel 201 to narrow compared to other sections of the microfluidic channel that are uncompressed. Arrows are shown in FIG. 2 to represent the flow of fluidic medium in the microfluidic channel 201.

Microfluidic channel 201 is shown in the cross-sectional view of FIG. 2 to be sandwiched at certain positions between metal electrodes. In other embodiments, the electrodes are attached to the inside walls of the microfluidic channel and when flexed to the inside of the channel, the wall of the channel moves internally with the flexed electrode. In the embodiment shown in FIG. 2, the electrode presented below the lower wall of the microfluidic channel represents a ground electrode 202 and is flexible to be movable in the vertical direction stressing against the section of the microfluidic channel 201 adjacent to ground electrode 202. Ground electrode 202 is shown to be below the microfluidic channel 201 in the embodiment of FIG. 2, however, it is to be understood that the positioning of the ground electrode 202 is not restricted to such orientation.

By way of non-limiting example, ground electrode 202 may be made from material such as Indium tin oxide (ITO), Gold, Chromium (Cr), or any other materials used in MEMS membrane or movable electrodes technologies. The vertical movement of the ground electrode 202 against the wall of microfluidic channel 201 adjacent to it causes the spacing inside the microfluidic channel 201 to narrow. Details of the vertical movement of the ground electrode 202 and the dynamic of the structure will be described in detail below.

The cross-sectional view of FIG. 2 also shows an electrodes array 203 present at the other side of the microfluidic channel 201 opposite to flexible electrode 202. In other embodiments, electrodes array may be on the inside of and coupled to the microfluidic channel. In FIG. 2, electrodes array 203 is shown to be fixed and non-flexible. By way of non-limiting example, electrodes array 203 may be made from material such as ITO, Gold, Cr, or any other materials used in MEMS fixed electrodes technologies. As electrodes array 203 is fixed and non-flexible, this means that the narrowing of the microfluidic channel 201 is only caused substantially due to movement of the ground electrode 202 against the wall of the microfluidic channel adjacent to the ground electrode 202.

The fixed electrodes array 203 and the ground electrode 202 are electrically connected to an electrical analyser 204. A potential difference is applied between individual electrodes of the fixed electrodes array 203 and ground electrode 202, with ground electrode 202 acting as ground. This creates an electrical field in the region of microfluidic channel 201 sandwiched between the two electrode layers.

Electrical analyser 204 may be used to measure different electrical properties of the fluidic medium inside the microfluidic channel 201 and any particles carried therein. Such electrical properties may be any of electrical impedance, phase, capacitance, current, charging or discharging responses. It is to be understood that other electrical properties known in the art may be detected by the electrical analyser 204 in the embodiment described in FIG. 2 and that different electrical conditioning may be applied across the electrodes arrays to allow for the measuring of such electrical properties.

Figure 3:
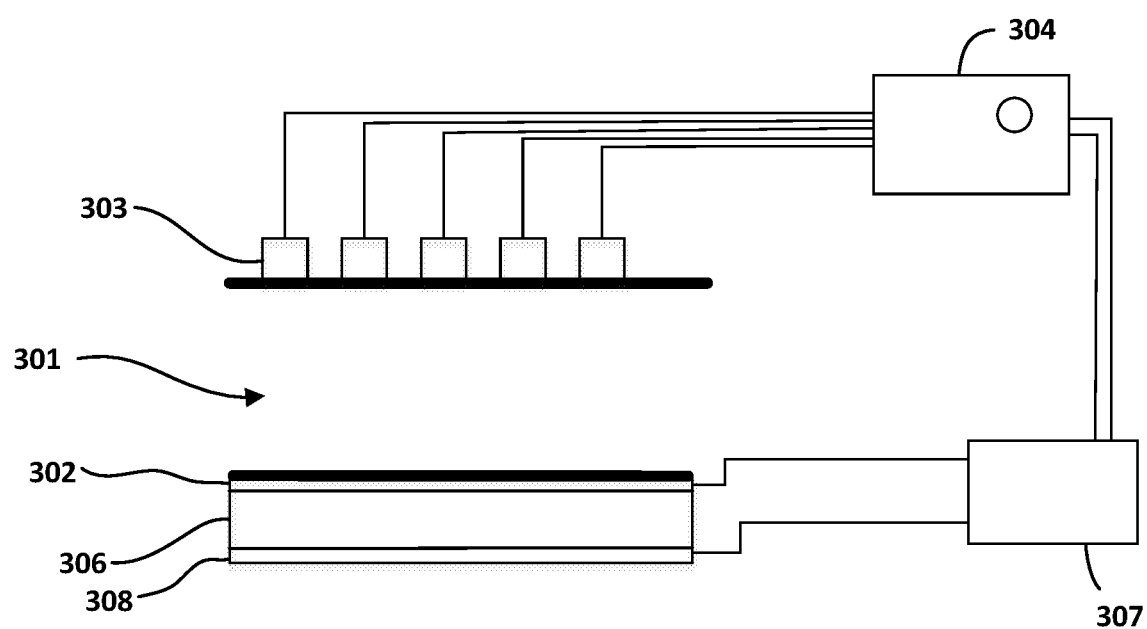
FIG. 3 shows a cross-sectional view of a sensor device utilizing microfluidic channels according to a second exemplary embodiment of the present invention.
Figure 4:
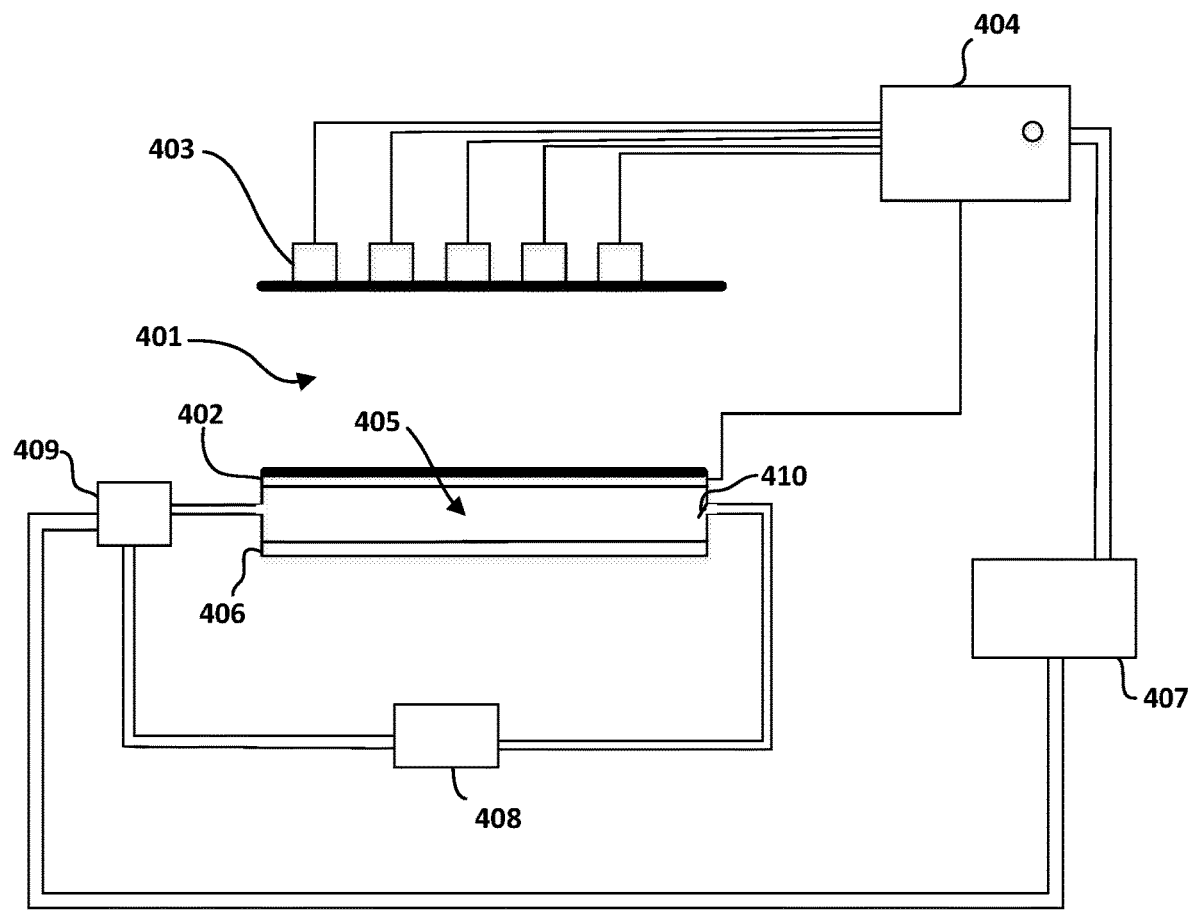
FIG. 4 shows a cross-sectional view of a sensor device utilizing microfluidic channels according to a third exemplary embodiment of the present invention.

The vertical actuation of the ground electrode 202 in the micro-sensing structure 101 may be caused using different techniques. Examples of such techniques are DC biasing, hydraulic pressure as well as through use of piezoelectric material. FIGS. 2-4 provide example embodiments where different actuation mechanisms are used to move the flexible ground electrode 202 in the system.

In FIG. 2, DC biasing techniques are shown to cause the movement of the flexible ground electrode 202 against the adjacent section of the microfluidic channel 201. Specifically, in FIG. 2 an electrode 205 is provided on the side of the flexible electrode 202 away from the microfluidic channel 201. Electrode 205 is fixed on a substrate 206, which may be made from non-conductive material such as PDMS, Glass, Si or any other sacrificial materials used in MEMS/NEMS and micromachining technologies. Electrode 205 may be made from ITO, Gold, Cr, or any other materials used in MEMS fixed electrodes technologies.

A potential difference is created between flexible ground electrode 202 and electrode 205, where flexible electrode 202 acts as ground. When the potential difference is created between electrodes 202 and 205, this causes the DC biasing between electrodes 202 and 205, which in turn causes the movement of flexible electrode 202 away from electrode 205. This in turn causes flexible electrode 202 to press against the wall of the microfluidic channel 201 adjacent to flexible electrode 202, which causes the narrowing of microfluidic channel 201 in that region. Circuits such as the ones used for MEMs DC biasing may be used in this embodiment; however, it is to be understood that any circuitry known in the art to cause such DC biasing may be used.

The DC biasing of flexible electrode 202 is controlled by a DC biasing controller 207. In some embodiments like the one presented in FIG. 2, DC biasing controller 207 is a separate controller unit from master controller 104 and is configured to control the voltage difference between flexible electrode 202 and fixed electrode 205. Any controller known in the art for configuring DC biasing may be used. By varying the voltage difference, the distance between flexible electrode 202 and fixed electrode 205 may be controlled by the DC biasing controller. This in turn allows for controlling the narrowing of the microfluidic channel 201 in the corresponding region of the flexible electrode.

It should be noted that by making flexible electrode 202 as ground, this minimizes electrical fluctuation between controller 207 (or master controller 104) and electrical analyser 204. This in turn allows for accurate measurements and minimises SNR in readings obtained from the micro-sensors.

In other embodiments, the DC biasing of flexible electrode 202 may be controlled by the master controller 104, which is also used to control the main pump 102 of system 100. In such embodiments, the controlling of the pumping pressure flow in main pump 102 and the DC biasing of flexible electrode 202 may be related or it may be independent from one another.

FIG. 3 shows a cross sectional view of another embodiment of the current disclosure in which on one side of the microfluidic channel 301, the flexible electrode layer 302 sandwiches a piezoelectric sheet 306 with a second electrode layer 308 away from the wall of the microfluidic channel 301, which is adjacent to the flexible electrode layer 302. In this embodiment, electrode layer 302 is grounded. Similar to the embodiment in FIG. 2, as seen in the cross section in FIG. 3, electrodes array 303 is positioned on the other side of the microfluidic channel 301 opposite the flexible electrode 302.

The fixed electrodes array 303 and the ground electrode 302 are connected to an electrical analyser 304. A potential difference is applied between individual electrodes of the fixed electrodes array 303 and ground electrode 302, with ground electrode 302 acting as ground. This creates an electrical field in the region of microfluidic channel 301 sandwiched between the two electrode layers. Electrical analyser 304 may be used to measure different electrical properties of the fluidic medium inside the microfluidic channel 301 and any particles carried therein. Such electrical properties may be any of electrical impedance, phase, capacitance, current, charging or discharging responses. It is to be understood that other electrical properties known in the art may be detected by the electrical analyser 304 in the embodiment described in FIG. 3 and that different electrical conditioning may be applied across the electrodes arrays to allow for the measuring of such electrical properties.

The actuation of the flexible electrode 302 may be induced by the application of potential difference between the ground layer 302 and the second electrode 308. This voltage difference may be applied by a controller 307.

The physical properties of piezoelectric material 306 allowed for the transformation of electrical energy provided by controller 307 into kinetic energy in the form of expansion of the piezoelectric layer 306. With the non-flexible electrode layer 308 restricting movement of piezoelectric layer 306 in its direction, piezoelectric layer 306 is moved in the other direction causing grounded flexible electrode layer 302 to actuate and press against the section of the microfluidic channel adjacent to flexible electrode 302. This in turn causes the narrowing of the spacing between the walls of the microfluidic channel section sandwiched between electrodes 302 and 303.

Any controller known in the art for applying the potential difference across the piezoelectric material may be used. By varying the voltage difference, the degree of movement of the piezoelectric layer is affected. This in turn allows for controlling the narrowing of the microfluidic channel 301 in the corresponding region of the flexible electrode 302.

In should be noted that in some embodiments, the potential difference applied between the piezoelectric layers 302 and 306 may be controlled by the master controller 104 instead of being controlled by a controller separate from the master controller 104. In either case, the controlling of the pumping of the fluidic medium by main pump 102 and the actuation of the flexible grounded electrode 302 be may configured either by the same processor or different processors to allow for synchronization of such controls as will be described below.

It should be noted that by making flexible electrode 302 as ground, this minimizes electrical fluctuation between controller 307 (or master controller 104) and electrical analyser 304. This in turn allows for accurate measurements and minimises signal to noise ratio (SNR) in readings obtained from the micro-sensors.

FIG. 4 shows a cross sectional view of another embodiment of the current disclosure in which fluidic pressure is used to actuate the flexible ground electrode 402. In this embodiment, on one side of the microfluidic channel 401, a flexible electrode 402 is provided. Flexible electrode 402 also forms a side of a second fluidic channel 405 with the other side of the second fluidic channel being a fixed non-flexible surface or electrode 406. Electrodes array 403 is positioned on the other side of the microfluidic channel 401 opposite the flexible electrode 402.

The fixed electrodes array 403 and the ground electrode 402 are electrically connected to an electrical analyser 404. A potential difference is applied between individual electrodes of the fixed electrodes array 403 and ground electrode 402, with ground electrode 402 acting as ground. This creates an electrical field in the region of the microfluidic channel 401 sandwiched between the two electrode layers. Electrical analyser 404 may be used to measure different electrical properties of the fluidic medium inside the microfluidic channel 401 and any particles carried therein. Such electrical properties may be any of electrical impedance, phase, capacitance, current, charging or discharging responses. It is to be understood that other electrical properties known in the art may be detected by electrical analyser 404 in the embodiment described in FIG. 4 and that different electrical conditioning may be applied across the electrodes array to allow for the measuring of such electrical properties.

In order to actuate the flexible electrode 402 in this embodiment, a secondary pump 409 is used to pump fluid through fluidic channels from fluid storage 408 into the second microfluidic channel 405 while at the same time restricting exit of such fluid from the second microfluidic channel 405 by closing a fluidic gate 410 of the second microfluidic channel 405. A controller 407 is used to control the pumping action of the fluid into the second microfluidic channel 405 as well as the closing and opening of the fluidic gate 410. This controller may be the same or different controller from master controller 104 in system 100 described in FIG. 1. Any fluid may be used in this embodiment in order to cause hydraulic pressure to build up inside second chamber 405.

When the fluid is pumped by secondary pump 409 into second microfluidic channel 405, controller 407 also closes the fluidic gate 410. This transforms the second microfluidic channel 405 into a fluidic chamber. As such, this allows the fluid being pumped into second microfluidic channel 405 to accumulate inside the fluidic chamber. With the continued pumping of fluid into the chamber, the chamber is caused to fill up and press against the flexible electrode 402 to accommodate for the change in volume. Therefore, hydraulic pressure is used in this embodiment to actuate the flexible electrode 402 to stress against the wall of the microfluidic channel 401 adjacent to the flexible electrode 402. This in turn allows for the concaving of the microfluidic channel 401 in this region and for narrowing the spacing inside microfluidic channel 401 in the region sandwiched between electrodes layers 402 and 403.

Controller 407 may also be used to open the fluidic gate 410, which will allow fluid to escape the second microfluidic channel 405. This will cause the hydraulic pressure inside the second microfluidic channel to reduce, which in turn will cause the flexible electrode 402 to move back to its unflexed configuration. This would ultimately lead to returning the spacing between the fixed electrodes 403 and flexible electrode 402 to the original spacing before hydraulic pressure was applied.

FIG. 4 shows that secondary pump 409, fluid storage 408 and second microfluidic channel 405 are in fluid communication with one another and are formed in a closed system. However, it is to be understood that the system may also be an open system, where once fluid leaves the second microfluidic channel 405, such fluid is disposed of and is not recycled back to the fluidic storage 408. In such embodiment, fluidic storage 408 may be supplied by fluid to maintain flow of such fluid into the second microfluidic channel 405.

Any controller known in the art may be used to control and synchronize the secondary pump 409 and the movement of the fluidic gate 410.

In some embodiments, hydraulic actuation of the flexible electrode 402 may be achieved without use of a fluidic gate 410. In such embodiments, secondary microfluidic channel 405 may be configured to be wider where the fluid enters the channel and narrower where the fluid exits the channel. In such embodiments, by increasing the fluidic flow using controller 407 (or master controller 104) and secondary pump 409, the rate of entrance of the fluid into secondary channel 405 may be controlled to be more than the rate of escape of the fluid from the channel. This creates an increase in fluidic volume inside secondary channel 405. This in turn causes flexible electrode 402 to flex outwardly from the secondary microfluidic channel 405 to accommodate the increase in fluidic volume inside the channel.

Returning to FIG. 2, the dimension and geometry of the internal hollow structure of microfluidic channel 201 is related to the dimensions of the particles carried by the fluidic medium inside the microfluidic channel 201. Specifically, the internal hollow structure of microfluidic channel 201 in the embodiment provided in FIG. 2 is dimensioned to be bigger in diameter than the size of the particle of interest, when the flexible electrode 202 is not stressed against the wall of the microfluidic channel. In some embodiments, the diameter of microfluidic channel 201 may be between several micro-meters to several thousand micrometers.

When the flexible electrode 202 is stressed against the wall of the microfluidic channel causing it to concave internally into the microfluidic channel 201, the narrowed spacing of the internal hollow structure of the microfluidic channel 201 is dimensioned to be substantially the same size as the particle of interest. This in turn causes a tight fit for the particle between the flexible electrode 202 and the fixed electrodes array 203.

It is to be understood that the system is designed to detect and analyse properties of different particles such as viruses, cells and exosomes and other organic and non-organic material. Therefore, it is contemplated that the narrowed spacing between electrodes 202 and 203 will be sufficient to cause a tight fit of such particles carried in the fluidic medium in the microfluidic channel. Size of such particles can range from few nano-meters to tens of micro-meters.

Figure 5:
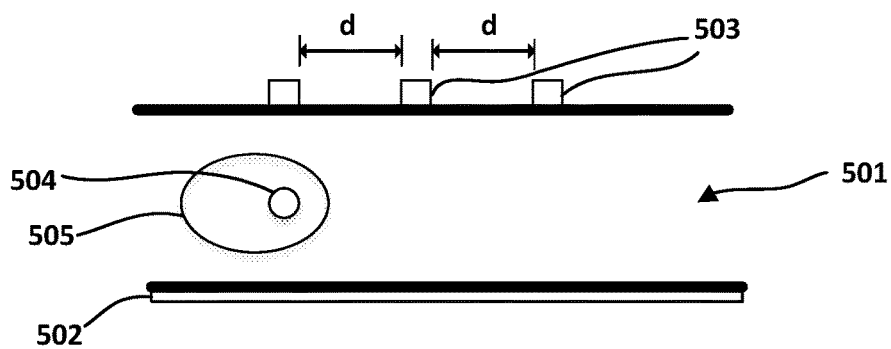
FIG. 5 shows a cross-sectional view of the microfluidic channel in FIG. 2 with a biological cell positioned in the microfluidic channel.
Figure 6:
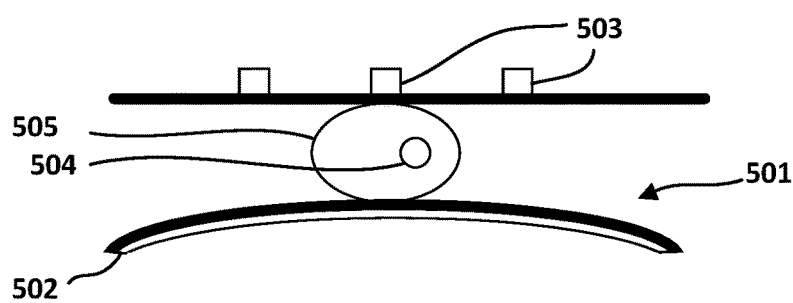
FIG. 6 shows a cross-sectional view of the microfluidic channel in any of FIGS. 2 to 4 having cell therein and where the flexible membrane is moved to press the cell against the fixed side of the microfluidic channel.

FIG. 5 shows a partial cross-sectional view of a microfluidic channel 501 containing a cell 505, where the walls of microfluidic channel 501 sandwiched between electrode arrays 503 and electrode layer 502 are not stressed by the flexible electrode 502. FIG. 6 shows a partial cross-sectional view of the microfluidic channel of FIG. 5, where the walls of microfluidic channel 501 are stressed by the flexible electrode 502 to cause a tight fit of the cell 505.

Figure 7:
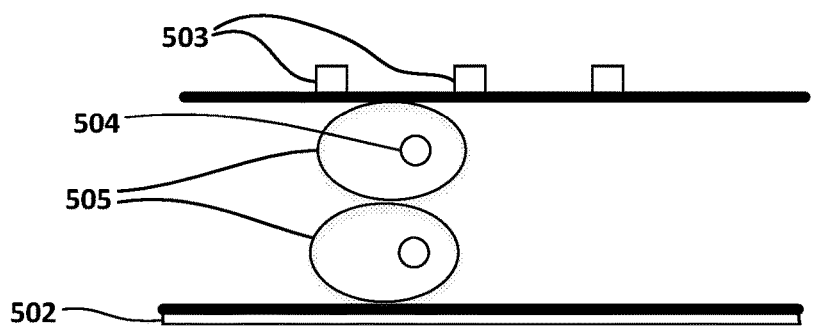
FIG. 7 shows a partial cross-sectional view of the microfluidic channel in any of FIGS. 2 to 4 having more than one cell oriented side by side to one another.

In a fluidic medium, it is possible for multiple particles to be present in a vertical orientation (or side by side) to one another such as seen in FIG. 7. In the case of the particles being cells, for example, presence of more than one cell side by side to one another may be due to mitosis. Another reason could be simply due to the size of diameter of the microfluidic channel being large enough to allow for more than one cell to flow side by side in the fluidic medium inside the microfluidic channel.

Figure 8:
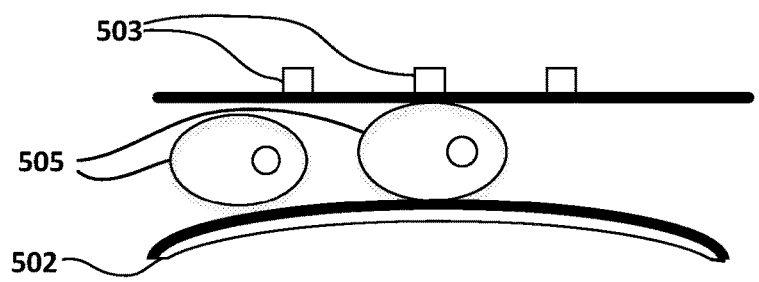
FIG. 8 shows a partial cross-sectional view of the microfluidic channel in FIG. 7 having the cells aligned in series in the direction of fluidic flow after the microfluidic channel is pressed by the flexible electrode.

Another function of the concaving action of the wall of the microfluidic channel adjacent to the flexible electrode is to align the particles of interest carried in the fluidic medium such that only one particle is captured in a tight fit configuration between the fixed electrodes and the flexible electrode sandwiching the microfluidic channel, such as seen in FIG. 8. To obtain such result, in some embodiments, multiple sections of flexible electrodes 402 are configured in series on one side of the microfluidic channel such that a first flexible electrode is utilized to align any particles that are oriented side by side in the fluidic medium and to re-arrange such particles to form in series to one another in the direction of fluidic flow. Alternatively, this action may be performed by one flexible electrode 402 stressing against the wall of the microfluidic channel adjacent to such flexible electrode.

It is to be understood that the flexibility of flexible electrode 202 in FIG. 2 allows for capturing different particles (one at a time), where the particles are of different sizes and shapes. Therefore, it is contemplated by this disclosure that the fluidic medium may have more than one type of particle and that such particles may have difference sizes and shapes.

Figure 9A:
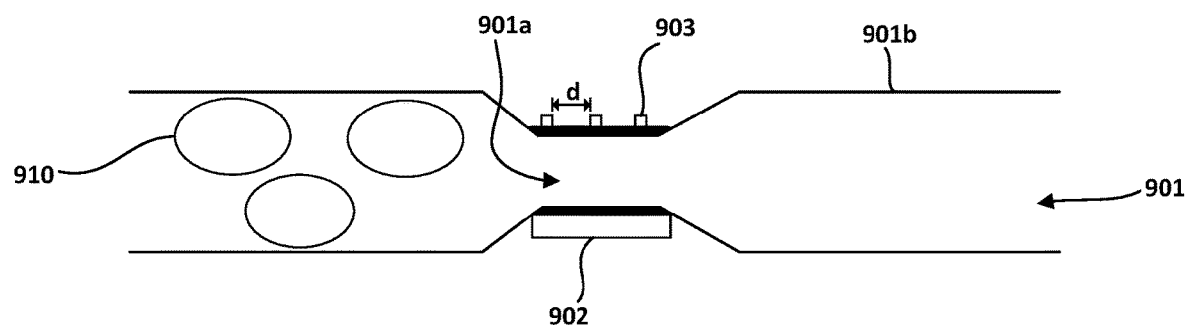
FIGS. 9A and 9B show a partial cross-sectional view of a microfluidic channel to be used in a sensor device according to another embodiment of the invention.
Figure 9B:
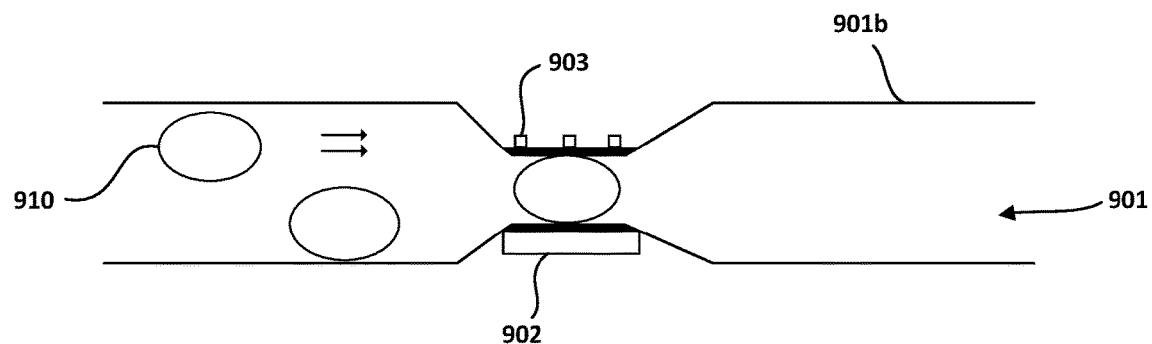

In some embodiments, where the type and size of a particle is known in a fluidic medium, the system may be designed such that no flexible electrode is needed and such that the walls of the microfluidic channel are not flexible. FIG. 9A shows such an embodiment. In such embodiments, a microfluidic sensor may include a nonflexible microfluidic channel 901. The width of the microfluidic channel would allow the fluidic medium with the particles 910 therein to pass through it. In such embodiments, the microfluidic channel would have a narrow section 901a and a wide section 901b. The wide section 901b may be dimensioned to be more in diameter than the particle's known size and the narrow section may be dimensioned to be less in diameter than the particle's known size. As the fluidic medium is pumped through the microfluidic channel (see FIG. 9B), as shown by the arrows, the particles in the fluid will reach the narrow section. As most biological structures are not rigid in shape, once a particle reaches the narrow section, and subject to the pressure pumping pressure of the pump in the system, the particles will be pushed into the narrow section. At that point, the narrow section would serve two purposes.

First, the narrow section would serve as a mechanism for aligning any neighboring particles in series one after the other since only one would be able to tightly fit at a time into the narrow section. Second, as the width of the narrow section is less than the diameter of the particle at its uncompressed stated, when the particle is pushed into the narrow section, it is captured by the walls of the narrow section.

An array of electrodes 903 may be coupled to a first section of the narrow section 901a of the microfluidic channel 901. The array of electrodes 903 may be similar to that described above in the other embodiment such that the array may have spacing "d" between each electrode of the electrodes array 903. Also, a ground electrode 902 may also be coupled to a second section of the narrow section 901a of the microfluidic channel 901 opposite to the array of electrodes. The structure and dynamics of all remaining elements in this embodiment would follow the same description provide for the other embodiments.

Returning to FIG. 2, the structure of the electrodes array 203 will now be described in detail. FIG. 2 shows the spacing between the electrodes in electrodes array 203 to be uniform. This is also seen in FIG. 5, where the spacing between electrodes 503 is presented by "d". By applying potential difference between one electrode and the next electrode in the array, the electrical field distribution is controlled inside the microfluidic channel.

In some embodiments, where the particle of interest is a cell, the electrode spacing is contemplated to be smaller than the size of the cell in order to allow for sectional scanning of the cell to identify structures 504 inside the cell, such as the cell nucleus or other particles inside the cell such as exomes, bacteria or viruses. In some embodiments, where the particle of interest is a virus or exosome, which may reside in a cell or may otherwise be carried separately in the fluidic medium, the electrode spacing is contemplated to be less than or as big as the size of such particle of interest. Therefore, it is to be understood that electrode spacing in electrodes array 203 may be between few nano-meters and several hundred nano-meters.

It should be noted that while the above has referenced FIG. 2 specifically in describing the capturing of the particle of interest inside microfluidic channel, the same is to be understood to apply in the case of embodiments provided in FIGS. 3 and 4.

As provided above, when the particles of interest are aligned in series in the microfluidic channel, this allows for one particle of interest to be captured at a time between the flexible electrode and the fixed electrode sandwiching a section of the microfluidic channel. When the particle of interest is captured, the flow of fluidic medium inside the narrowed microfluidic channel is slowed down to a stop.

When the particle is captured and stopped by the tight fit of the reshaped (narrowed) microfluidic channel, electrical properties of the captured particle may be measured between each two adjacent electrodes in the electrodes array 203. In the case of the particle of interest being a cell, as the electrode spacing is smaller than the size of the cell, conditioning of electrical properties between adjacent electrodes will allow for measuring of electrical properties of a section of the cell positioned between the two adjacent electrodes. This may be used to represent spatial measurements of the cell's electrical properties.

Referring to FIGS. 1 and 2, the pressure flow of the fluidic medium inside the microfluidic channel is controlled by the master controller 104, which controls the pumping action of main pump 102 in system 100. Therefore, master controller 104 is responsible for setting up the initial pressure flow of the fluidic medium into microfluidic channel 201. When the cell, carried in the fluidic medium, is captured by the tight fit caused to the microfluidic channel 201 between electrodes 202 and 203, the pressure applied on the cell by the tight fit action of electrodes 202 and 203 counterbalances the initial pressure flow from the fluidic medium. This causes the cell captured to be stopped. This in turn allows for the sectional scanning of the cell while stationary by measuring its electrical properties between adjacent electrodes of electrodes array 203.

The measurement of the electrical properties between adjacent electrodes in electrodes array 203 may take several minutes to few hours to complete. During this time, the master controller 104 is configured to maintain the same pressure flow of fluidic medium inside the microfluidic channel. In some embodiments, where the master controller 104 also controls the movement of the flexible electrode, which in turn causes the tightening of the spacing of the microfluidic channel sandwiched by electrodes 202 and 203, both controls may be configured so that the captured cell is held stationary until the measurement of the electrical property of the section of the cell is complete.

Once the electrical measurement is completed between two adjacent electrodes of electrodes array 203, the master controller 104 may be configured to cause the main pump 102 to increase the pressure flow of the fluidic medium in the microfluidic channel 201 while maintaining the pressure exerted by the flexible electrode 202 on the cell, in the direction perpendicular to the direction of fluidic flow, the same. This in effect causes the cell to be pushed through the tight fit spacing created by the fixed electrode 203 and the flexible electrode 202.

In order to allow for measurement of the same electrical properties for a next section of the captured cell between the same two adjacent electrodes in electrodes array 203, the distance the captured cell is moved through the tight fit spacing is contemplated to be equivalent to one full spacing "d" between electrodes in electrodes array 203. In some embodiments, spacing "d" may be 100 nano-meter or a size proportional to a size of a virus or an exosome.

Once the cell is pushed such distance, the pressure flow of the fluidic medium may be reduced to its original value. This in turn will allow the cell to be held stationary again. This will allow the two adjacent electrodes in electrodes array 203 to measure the same electrical properties but for the new section positioned between them due to the movement of the cell through the tight fit spacing. This process will be repeated after each completed measurement of electrical properties of a section of the cell until the desired electrical properties of all sections of the cell have been measured.

The action of controlled movement of the cell through the tight fit spacing of the sandwiched microfluidic channel may be described as discrete movement of the cell. By knowing the distance traveled by the cell through the tight fit spacing as well as the time the cell is held stationary between movement actions, and the dimension of measure particle, the pressure flow required to cause the discrete movement may be determined.

In the case of all embodiment described, the following equation may be used to determine the horizontal force applied to a particle stopped by the flexed electrodes:

$$F_h = \frac{mQ^2}{2x(\pi r)^2} \quad (1)$$

Where: m represents the average mass of a cell; r represents the radius of mass (assuming the cell is substantially spherical). At the narrowed region of the microfluidic channel, r also represents twice the width of the microfluidic channel. Q represents the flow rate; and x represents the distance the cell travels from the beginning of the microfluidic channel and until the point it has stopped, which in some embodiments may be represented by half the length of the flexible sheet.

The vertical force applied to the particle stopped by the flexed electrodes in FIG. 2 are presented by:

$$F_v = \frac{\varepsilon_o \varepsilon_e A V^2}{2y^2} + mg \quad (2)$$

Where $\varepsilon_o$ is the dielectric constant for free space; $\varepsilon_e$ is effective dielectric constant between two electrodes; A is the cross-sectional area of the electrode sheet; V is the DC voltage applied; y is the vertical displacement of the flexible electrode sheet; m is the mass of the cell; and g is gravity.

The vertical force applied to the particle stopped by the flexed electrodes in FIG. 3 are presented by:

$$Fv = \frac{LWV}{Tg_p} + mg \quad (3)$$

Where L is the length of the piezoelectric sheet; W is width of the piezoelectric sheet; T is the thickness of the piezoelectric sheet; $g_p$ is the piezoelectric constant based on potential applied to the sheet; m is the mass of the cell and is considered a constant for known cells; g is gravity; and V is voltage potential applied to the piezoelectric sheet.

In embodiments where movement of the flexible electrode is controlled by a controller different from the master controller 104, coordination may be established between such controller and the master controller to allow for holding of the captured cell in position until measurement of electrical properties of a section of the cell is completed between two adjacent electrodes of the electrodes array and to also control the discrete movement of the cell through the tight fit spacing of the microfluidic channel sandwiched by the fixed and flexible electrodes to allow for obtaining similar measurements for other sections of the cell. Such coordination may be done by way of non-limiting example through linking of the processors programming the separate controls in the system.

Automation of the system in any of the embodiments described above may be established through the use of a general processor that is configured to control either through one or more controllers:

1) the initial flow of the fluidic medium into the microfluidic channel;
2) the movement of the one or more flexible electrode for aligning particles of interest in series in the direction of fluidic flow;
3) the capturing of the particles of interest one at a time through the tight fit caused by the movement of the flexible electrode against the walls of the microfluidic channel;
4) the fluctuation in flow of the fluidic medium in the microfluidic channel following the capture of the particle of interest to cause it to move discrete movements;
5) the measuring of electrical properties of sections of the particle of interest disposed between the electrode spacing of the electrodes in the electrodes arrays on one side of the microfluidic channel, while the particle of interest is held stationary; and
6) the feedback process between the electrodes, analyser and controllers.

Referring back to FIG. 1, system 100 may be subject to manual operation, where the controller is powered manually after depositing the fluidic sample containing the particles of interest into the depositing chamber. Similarly, when the fluidic sample is completely passed though the micro-sensing structure 101, the user may manually stop the controller, which would cause the system to shut down and cease operating.

In another embodiment, the operation of when the system starts and stops may be automated. This may for example be established by providing sensors in the depositing chamber 103 for detecting fluid in the chamber. When the sensors detect such fluid, the sensors communicate to the controller the presence of sample fluid to be processed, which in turn causes the controller to operate the pump to pump the fluid into the micro-sensing structure. When the sample fluid is depleted from the depositing chamber, the sensors communicate to the controller to stop the pumping action of the sample fluid into the micro-sensing structure 101, thereby stopping operation of the system 100.

Use of the system described above may be established in the medical field. By way of non-limiting example, and referring to FIGS. 2 and 5, a control sample may be used in which the fluidic medium, cells and other particles of interest therein are known. Electrical parameters such as capacitance may be measured between electrode spacing "d" of electrodes 203 for the fluidic medium, the known cells carried in the fluidic medium as well as the other known particles of interest such as viruses, exosomes, bacteria or other organic material disposed inside the cells or carried separately in the fluidic medium. The spacing between electrodes 203 being proportional to the size of a virus or an exosome allows for obtaining measurements corresponding to each of these particles in the controlled sample.

A lookup table may be generated for each of the known cells and its composition effective electrical parameters (such as capacitance in this example). The same may also be generated for viral particles as well as other particles of interest disposed inside the known cell or carried separately in the fluidic medium. Different viruses may be provided to allow for obtaining different measurements of electrical properties for the different viruses.

Once the lookup table is generated using different control samples containing a variety of particle of interest, a sample of uncontrolled content such as fresh blood sample, disposed in a known fluidic medium, may be examined using the system described in this current disclosure. The electrical parameter (such as capacitance for example) may then be measured for sections of the particles disposed in the fluidic medium, such as blood cells.

The electrical parameter (such as capacitance) measured for the uncontrolled sample may then be compared to values in the lookup table. Based on the assumption that the distribution of abnormalities is not uniform in a cell, it is contemplated that through the sectional spatial scanning by system 100 of particles and cells, electrical properties of sections of cells will be measured, where no abnormalities are present. Such measurements, will help identify the type of cells measured when compared to the values in the lookup table.

Once the cell is identified, abnormalities, such as viruses or other particles of interest may be identified in the cell by comparing the electrical property measurements for sections of the cell with the lookup table. For example, in the event a varied capacitance is measured for a known cell in a fluidic medium, and that varied capacitance matches an entry in the lookup table representative of a capacitance value of a virus, then the lookup table may be used to establish the presence of that virus in the cell under examination. This process may be repeated to identify more than one virus in a cell through analysis of each sectional measurement of the cell.

Also, given that the capacitance of multiple viruses of the same type in a single cell is considered parallel capacitance, then capacitance of multiple viruses of the same type in a cell is added. As such, by reversing this process, the number of viruses of the same type in an infected cell may be established in an identified cell.

Furthermore, based on the measured spatial capacitances, the effective dielectric constant may be extracted, which can be used for identifying the particle being detected inside the cell of interest.

The system described in this disclosure may be used to distinguish between cells expressing abnormalities such as viruses from cells that do not express such abnormalities. Such system and technique may be utilised in production of a lab-free, electrical detection of virally infected cells in biological samples and individuals for diagnostic purposes. In some embodiments, the system may include a memory storage device, which may be integral to the processor of the system or separate therefrom. The lookup table may be stored on such storage device and accessed by the processor of the system in order to obtain values for comparison with measured values of electrical properties. Such measurements may be used to identify cells as well as abnormalities in the cells as described above.

The system and method described in this current disclosure allow for detections of abnormalities in a cell in a short period of time compared to the traditional techniques. They also allow for establishing such objective with relative accuracy and without use of costly equipment.

Interpretation of Terms

Unless the context clearly requires otherwise, throughout the description and the claims:
"comprise," "comprising," and the like are to be construed in an inclusive sense, as opposed to an exclusive or exhaustive sense; that is to say, in the sense of "including, but not limited to".
"connected," "coupled," or any variant thereof, means any connection or coupling, either direct or indirect, between two or more elements; the coupling or connection between the elements can be physical, logical, or a combination thereof.
"herein," "above," "below," and words of similar import, when used to describe this specification shall refer to this specification as a whole and not to any particular portions of this specification.
"or," in reference to a list of two or more items, covers all of the following interpretations of the word: any of the items in the list, all of the items in the list, and any combination of the items in the list.
the singular forms "a", "an" and "the" also include the meaning of any appropriate plural forms.
"subject" refers to a human or other animal. It is intended that the term encompass patients, such as vocally-impaired patients, as well as inpatients or outpatients with which the present invention is used as a diagnostic or monitoring device. It is also intended that the present invention be used with healthy subjects (i.e., humans and other animals that are not vocally-impaired, nor suffering from disease). Further, it is not intended that the term be limited to any particular type or group of humans or other animals.
"power source" and "power supply" refer to any source of electrical power in a form that is suitable for operating electronic circuits.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", "upper", "lower" and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of device and method have been described herein for purposes of illustration. These are only examples. The technology provided herein can be applied to device and method other than the examples described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:

1. A microfluidic sensor for detecting a particle in a fluidic medium, the microfluidic sensor comprising:
   a microfluidic channel having a width through which the fluidic medium is passed, the microfluidic channel having a flexible membrane;
   an array of non-flexible electrodes coupled to a first section of the microfluidic channel; the array of non-flexible electrodes having spacing between each electrode of the array of non-flexible electrodes;
   a flexible electrode coupled to a second section of the microfluidic channel opposite to the array of non-flexible electrodes;
   an electrical analyser in electrical communication with each electrode of the array of non-flexible electrodes and the flexible electrode, the electrical analyser applying an electrical potential between each of the electrodes in the array of non-flexible electrodes to generate an electrical field inside the microfluidic channel with the flexible electrode acting as ground; and means for actuating the flexible electrode to narrow the width of the microfluidic channel between the first section and second section and to capture the particle between the first section and the second section of the microfluidic channel, at least one controller;

a processor in communication with the at least one controller and the electrical analyser;

a memory storing computer-executable instructions that, when executed by the processor, are to facilitate the microfluidic sensor to:

scan a section of the particle between two adjacent electrodes of the array of non-flexible electrodes while the particle is captured between the first section and the second section using the electrical field generated;

incrementally move the captured particle through the microfluidic channel and scan a next section of the particle between the two adjacent electrodes of the array of non-flexible electrodes using the electrical field generated after each incremental move until the particle entirely passes through and sectional scans for the particle are obtained; and use the sectional scans to detect and identify the particle.

2. The microfluidic sensor of claim 1 further comprising a pump for pumping the fluidic medium through the microfluidic channel to an area where the particle in the fluidic medium is captured.

3. The microfluidic sensor of claim 2, wherein the at least one controller is for controlling any one of the electrical potential applied by the analyser, volume flow of the fluidic medium, or rate of pumping the fluidic medium through the microfluidic channel.

4. The microfluidic sensor of claim 3, wherein the means for actuating the flexible electrode comprises an electrostatic electrode resting on a substrate away from the microfluidic channel, the electrostatic electrode in electrical communication with the at least one controller, the at least one controller applying an electrostatic biasing between the flexible electrode and the electrostatic electrode to cause the flexible electrode to flex and narrow the microfluidic channel.

5. The microfluidic sensor of claim 3, wherein the means for actuating the flexible electrode comprises a piezoelectric sheet sandwiched between the flexible electrode and a second electrode; the second electrode in electrical communication with the at least one controller, the at least one controller applying a potential difference between the second electrode and the flexible electrode causing the piezoelectric sheet to move thereby flexing the flexible electrode to narrow the microfluidic channel.

6. The microfluidic sensor of claim 3, wherein the means for actuating the flexible electrode comprises a second microfluidic chamber sandwiched between the flexible electrode and a fixed side; a second pump for pumping pressure fluid into the second microfluidic chamber, the second pump in electrical communication with the at least one controller, the at least one controller causing the flexible electrode to flex to narrow the microfluidic channel by controlling, through the second pump, flow rate, volume and timing of the pressure fluid into the second microfluidic chamber.

7. The microfluidic sensor of claim 3, wherein, the at least one controller is configured to control holding the cell stationary between the first section and the second section until the scan of the section of the particle is completed between the two adjacent electrodes; the at least one controller is further configured to control incremental movement of the particle through a tight fit spacing between the first section and the second section of the microfluidic channel to scan the next section of the particle and create the sectional scan of the particle.

8. The microfluidic sensor of claim 1, wherein the flexible electrode is configured to be displaced between a flexed configuration and a non-flexed configuration and wherein when the flexible electrode is in the non-flexed configuration, the microfluidic channel is dimensioned to be bigger in diameter than the particle and when the flexible electrode is in the flexed configuration, the microfluidic channel is dimensioned to be substantially equal in diameter to the particle causing a tight fit of the particle between the first section and second section of the microfluidic channel.

9. The microfluidic sensor in claim 8, wherein the particle is one of a virus, a cell, an exosome or other biological or non-biological material.

10. The microfluidic sensor in claim 1, wherein the spacing between each electrode of the array of non-flexible electrodes is uniform.

11. The microfluidic sensor in claim 10, wherein when the particle is a cell, the spacing is less than a diameter of the cell.

12. The microfluidic sensor in claim 10, wherein when the particle is one of an exosome, a bacteria or a virus, the spacing is substantially equal to the particle.

13. A method of detecting a particle in a fluidic medium using a microfluidic sensor, the method comprising the steps of:

passing the fluidic medium through a flexible microfluidic channel of the microfluidic sensor, the flexible microfluidic channel having an array of non-flexible electrodes uniformly spaced apart and coupled to a first section of the microfluidic channel, and a flexible electrode coupled to a second section of the microfluidic channel opposite to the array of non-flexible electrodes;

controlling the movement of the flexible electrode to narrow a width of the microfluidic channel and to capture the particle between the first section and the second section;

generating an electrical field between the electrodes of the array of non-flexible electrodes spaced apart;

scanning a section of the particle between two electrodes of the array of non-flexible electrodes while the particle is captured between the first section and the second section using the electrical field generated;

incrementally moving the captured particle through the microfluidic channel and scanning a next section of the particle between the two electrodes of the array of non-flexible electrodes using the electrical field generated after each incremental move until the particle entirely passes through and sectional scans for the particle are obtained; and using the sectional scans to detect and identify the particle.

14. The method of claim 13, further comprising the additional steps of:

using a plurality of control samples of fluidic medium, each having known particles therein;

generating sectional scans for the particle in each control sample; and storing the generated sectional scans comprising electrical properties of each particle in a lookup table.

15. The method of claim 14, further comprising the additional steps of:

identifying a particle in an unknown sample by comparing the sectional scans of the particle therein; and matching values of the sectional scans of the particle to values obtained from the lookup table.

* * * * *